(12) United States Patent
Seo et al.

(10) Patent No.: US 11,951,066 B2
(45) Date of Patent: Apr. 9, 2024

(54) WALKING ASSISTANCE METHOD AND APPARATUS

(71) Applicant: Samsung Electronics Co., Ltd., Suwon-si (KR)

(72) Inventors: Keehong Seo, Seoul (KR); Youngjin Park, Seoul (KR); Jusuk Lee, Hwaseong-si (KR); Hyundo Choi, Yongin-si (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1109 days.

(21) Appl. No.: 16/412,867

(22) Filed: May 15, 2019

(65) Prior Publication Data

US 2020/0085666 A1    Mar. 19, 2020

(30) Foreign Application Priority Data

Sep. 14, 2018   (KR) ........................ 10-2018-0109919

(51) Int. Cl.
*A61H 3/00* (2006.01)
*A61B 5/00* (2006.01)
(Continued)

(52) U.S. Cl.
CPC ................ *A61H 3/00* (2013.01); *A61B 5/112* (2013.01); *A61B 5/1121* (2013.01);
(Continued)

(58) Field of Classification Search
CPC ..... A61B 5/112; A61B 5/1121; A61B 5/6828; A61B 5/6829; A61B 5/7267;
(Continued)

(56) References Cited

U.S. PATENT DOCUMENTS

| 9,974,478 | B1* | 5/2018 | Brokaw ................ A61B 5/486 |
| 2009/0204230 | A1 | 8/2009 | Kaltenborn et al. |

(Continued)

FOREIGN PATENT DOCUMENTS

| KR | 10-1494779 B1 | 2/2015 |
| KR | 10-2015-0085357 A | 7/2015 |

(Continued)

OTHER PUBLICATIONS

Juri Taborri et al. "Gait Partitioning Methods: A Systematic Review", Sensors 2016, 16, 66; doi:10.3390/s16010066; www.mdpi.com/journal/sensors <http://www.mdpi.com/journal/sensors>; MDPI, Basel, Switzerland, pp. 1-20.

(Continued)

*Primary Examiner* — Margaret M Luarca
*Assistant Examiner* — Tyler A Raubenstraw
(74) *Attorney, Agent, or Firm* — Harness, Dickey & Pierce, P.L.C.

(57) ABSTRACT

A method and apparatus for assisting walking of a user is provided. Information related to a motion of a user wearing a walking assistance apparatus is measured by an inertial measurement unit (IMU), a gait phase of the user corresponding to the measured information is predicted using data learned in advance through machine learning, an assistance torque to be provided to the user is determined based on the predicted gait phase, and a driver is controlled to output the assistance torque.

18 Claims, 18 Drawing Sheets

(51) Int. Cl.
*A61B 5/11* (2006.01)
*A61H 1/02* (2006.01)

(52) U.S. Cl.
CPC .......... *A61B 5/6828* (2013.01); *A61B 5/6829* (2013.01); *A61B 5/7267* (2013.01); *A61B 5/7275* (2013.01); *A61H 1/0262* (2013.01); *A61B 2562/0219* (2013.01); *A61H 2003/007* (2013.01); *A61H 2201/5061* (2013.01); *A61H 2201/5084* (2013.01); *A61H 2205/10* (2013.01); *A61H 2230/625* (2013.01)

(58) Field of Classification Search
CPC .......... A61B 5/7275; A61B 2562/0219; A61H 3/00; A61H 1/0262; A61H 2201/5061; A61H 2201/5084; A61H 2205/10; A61H 2230/625; A61H 2003/007; B25J 9/0006
See application file for complete search history.

(56) References Cited

U.S. PATENT DOCUMENTS

| | | | | |
|---|---|---|---|---|
| 2010/0125229 | A1* | 5/2010 | Rudolph | A61H 3/008 600/595 |
| 2011/0295385 | A1 | 12/2011 | Herr et al. | |
| 2013/0296746 | A1* | 11/2013 | Herr | A63B 23/0405 601/34 |
| 2014/0100493 | A1* | 4/2014 | Craig | B25J 9/0006 601/35 |
| 2014/0180173 | A1* | 6/2014 | Sullivan | A61B 5/112 600/595 |
| 2014/0261887 | A1 | 9/2014 | Groot et al. | |
| 2014/0330431 | A1* | 11/2014 | Hollander | A61H 3/00 29/428 |
| 2014/0358290 | A1* | 12/2014 | Kazerooni | G06F 3/011 700/275 |
| 2015/0080979 | A1 | 3/2015 | Lasko et al. | |
| 2015/0081037 | A1 | 3/2015 | Langlois et al. | |
| 2015/0100135 | A1* | 4/2015 | Ives | A61B 5/6823 623/25 |
| 2015/0289995 | A1* | 10/2015 | Wilkinson | A61F 2/60 623/27 |
| 2016/0095538 | A1* | 4/2016 | Lee | A61B 5/112 600/595 |
| 2016/0113536 | A1* | 4/2016 | Greenhut | A61B 5/316 600/512 |
| 2016/0113831 | A1* | 4/2016 | Hollander | A61H 3/00 623/32 |
| 2016/0287463 | A1* | 10/2016 | Yue | A61H 1/0244 |
| 2016/0331557 | A1* | 11/2016 | Tong | A61F 2/6607 |
| 2017/0043213 | A1* | 2/2017 | Daumer | A61B 5/112 |
| 2017/0043476 | A1* | 2/2017 | Seo | G05B 19/042 |
| 2017/0181917 | A1* | 6/2017 | Ohta | A61H 1/0281 |
| 2017/0303826 | A1* | 10/2017 | Haraikawa | A61B 5/6801 |
| 2017/0319369 | A1* | 11/2017 | Han | A61F 5/0127 |
| 2018/0036147 | A1 | 2/2018 | Gregg et al. | |
| 2018/0085280 | A1* | 3/2018 | Shimada | A61H 1/024 |
| 2018/0092792 | A1* | 4/2018 | Ohta | B25J 9/1633 |
| 2018/0220937 | A1* | 8/2018 | Mizuochi | A61B 5/112 |
| 2018/0228684 | A1* | 8/2018 | Park | B62D 57/032 |
| 2018/0310859 | A1* | 11/2018 | Knabe | A61B 5/4528 |
| 2019/0125616 | A1* | 5/2019 | John | A61H 1/0244 |
| 2019/0209413 | A1 | 7/2019 | Lee et al. | |

FOREIGN PATENT DOCUMENTS

| | | | |
|---|---|---|---|
| KR | 2016/0089791 A | 7/2016 | |
| KR | 101642286 B1 | 7/2016 | |
| KR | 10-2017-0019175 A | 2/2017 | |
| KR | 101750717 B1 | 6/2017 | |
| KR | 101751760 B1 | 6/2017 | |
| WO | WO-2009089204 A2 * | 7/2009 | ............... A61H 3/00 |
| WO | WO-2019014152 A1 * | 1/2019 | ............... A61B 5/11 |

OTHER PUBLICATIONS

Notice of Preliminary Rejection dated Dec. 29, 2022 in Korean Application No. 10-2018-0109919.
Notice of Allowance dated Oct. 4, 2023 in Korean Application No. 10-2018-0109919.

\* cited by examiner

1200

WALKING ASSISTANCE METHOD AND APPARATUS

CROSS-REFERENCE TO RELATED APPLICATION

This application claims under 35 U.S.C. § 119 to Korean Patent Application No. 10-2018-0109919, filed on Sep. 14, 2018, in the Korean Intellectual Property Office, the entire contents of which are incorporated herein by reference in their entirety.

BACKGROUND

1. Field

At least one example embodiment relates to a method and/or apparatus for assisting walking of a user. For example, at least some example embodiments relate to a method and/or apparatus for providing an assistance force to assist walking when the user walks.

2. Description of the Related Art

With the onset of rapidly aging societies, an increasing number of people may experience inconvenience and/or pain from joint problems. Thus, there may be a growing interest in motion assistance apparatuses enabling the elderly and/or patients having joint problems to walk with less effort. Further, motion assistance apparatuses increasing muscular strength of users for military purposes are being developed.

SUMMARY

Some example embodiments relate to a walking assistance method.

In some example embodiments, the walking assistance method includes predicting a gait phase of a user within a gait cycle based on information received from a sensor, the information being related to a motion of the user wearing a walking assistance apparatus; and controlling an assistance torque applied to the walking assistance apparatus based on the gait phase.

In some example embodiments, the method further includes receiving, from the sensor, the information related to the motion of the user wearing the walking assistance apparatus, and wherein the gait phase includes information indicating a gait progress in a period corresponding to the gait cycle.

In some example embodiments, the predicting includes predicting data indicative of the gait phase by inputting the information into a trained neural network, the data being encoded to have a continuity on a boundary of the gait cycle; and determining the gait phase by decoding the data.

In some example embodiments, the method further includes encoding the data such that the data includes information indicating a vertex corresponding to the gait phase, among vertices on a circumference of a circle corresponding to the gait cycle, through a trigonometrical function.

In some example embodiments, the method further includes encoding the data such that the data includes information indicating a vertex corresponding to the gait phase, among a plurality of vertices included in a perimeter of a figure corresponding to the gait cycle.

In some example embodiments, the controlling includes determining the assistance torque based on the gait phase; and controlling a driver to output the assistance torque.

In some example embodiments, the determining the assistance torque includes determining a time to apply the assistance torque based on the gait phase; and determining a magnitude of the assistance torque based on the time.

In some example embodiments, the sensor is on a foot or a shank of the user.

In some example embodiments, the sensor includes an inertial measurement unit (IMU), and wherein the receiving includes receiving, from the IMU, one or more of acceleration information and rotation velocity information.

In some example embodiments, the motion of the user includes one or more of a level walking motion, a level running motion, a slope walking motion, and a slope running motion of the user.

Some example embodiments relate to a method of training a gait phase regression module (PRM).

In some example embodiments, the method includes receiving, from a first sensor, first information related to a motion of a user wearing a walking assistance apparatus; receiving, from a second sensor, second information related to the motion of the user; determining an initial gait phase within a gait cycle based on the first information and the second information; predicting a gait phase within the gait cycle by applying the first information to the gait PRM; and training the gait PRM based on the gait phase and the initial gait phase.

In some example embodiments, the gait phase includes information indicating a gait progress in a period corresponding to the gait cycle.

In some example embodiments, the predicting includes predicting data indicative of the gait phase by inputting the first information into the gait PRM, the data being encoded to have a continuity on a boundary of the gait cycle; and determining the gait phase by decoding the data.

In some example embodiments, the method further includes encoding the data such that the data includes information indicating a vertex corresponding to the gait phase, among a plurality of vertices included in a perimeter of a figure corresponding to the gait cycle.

Some example embodiments relate to a non-transitory computer-readable medium including computer readable instructions that, when executed by a computer, cause the computer to perform a walking assistance method.

Some example embodiments relate to a walking assistance apparatus.

In some example embodiments, the walking assistance apparatus includes a sensor configured to measure a motion of a user wearing the walking assistance apparatus; a driver configured to assist walking of the user; and at least one processor configured to, predict a gait phase within a gait cycle of the user based on information, and control an assistance torque applied to the walking assistance apparatus based on the gait phase.

In some example embodiments, the gait phase includes information indicative of a gait progress in a period corresponding to the gait cycle.

In some example embodiments, the processor is configured to, predict data indicating the gait phase by inputting the information into a trained neural network, the data being encoded to have a continuity on a boundary of the gait cycle, and determine the gait phase by decoding the data.

In some example embodiments, the processor is configured to encode the data such that the data includes information indicating a vertex corresponding to the gait phase, among a plurality of vertices included in a perimeter of a figure corresponding to the gait cycle.

In some example embodiments, the sensor includes an inertial measurement unit (IMU), the IMU being configured to measure one or more of acceleration information and rotation velocity information.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

The following structural or functional descriptions of example embodiments described herein are merely intended for the purpose of describing the example embodiments described herein and may be implemented in various forms. However, it should be understood that these example embodiments are not construed as limited to the illustrated forms.

Various alterations and modifications may be made to the examples. Here, the examples are not construed as limited to the disclosure and should be understood to include all changes, equivalents, and replacements within the idea and the technical scope of the disclosure.

Terms such as first, second, A, B, (a), (b), and the like may be used herein to describe components. Each of these terminologies is not used to define an essence, order or sequence of a corresponding component but used merely to distinguish the corresponding component from other component(s). For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

The terminology used herein is for the purpose of describing particular examples only, and is not to be used to limit the disclosure. As used herein, the terms "a," "an," and "the" are intended to include the plural forms as well, unless the context clearly indicates otherwise. As used herein, the terms "include, "comprise," and "have" specify the presence of stated features, numbers, operations, elements, components, and/or combinations thereof, but do not preclude the presence or addition of one or more other features, numbers, operations, elements, components, and/or combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Figure 1:
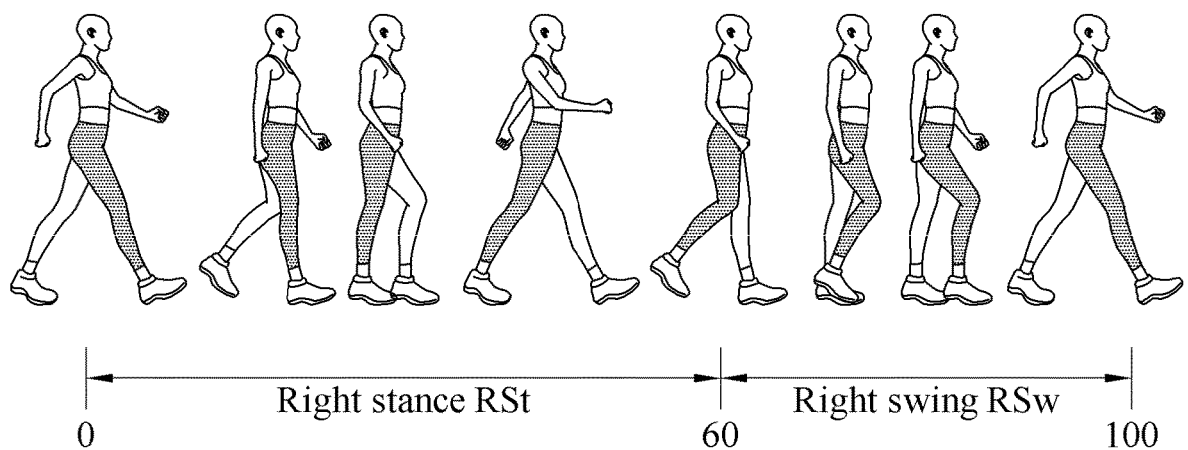
FIG. 1 illustrates gait states according to at least one example embodiment.

FIG. 1 illustrates gait states according to at least one example embodiment.

Gait phases of a leg of a user with respect to a gait may be predefined.

Referring to FIG. 1, gait phases may include discontinuous values classified into a stance and a swing. Gait phases of a left leg may include a left stance LSt and a left swing LSw. Gait phases of a right leg may include a right stance RSt and a right swing RSw.

The gait phases may have continuous values with respect to a gait progress from a predetermined start point to a predetermined end point. For example, a gait phase with respect to a stance may be a gait phase based on a stance. In detail, a gait phase 0% with respect to the stance may be mapped to a point in time at which the stance is started, a gait phase 60% with respect to the stance may be mapped to a point in time at which a swing is started, and a gait phase 100% with respect to the stance may be mapped to a point in time immediately before the stance is started. Similarly, a gait phase with respect to a swing may be a gait phase based on a swing. In detail, a gait phase 0% with respect to the swing may be mapped to a point in time at which the swing is started, a gait phase 60% with respect to the swing may be mapped to a point in time at which a stance is started, and a gait phase 100% with respect to the swing may be mapped to a point in time immediately before the swing is started. In another example, the gait phases may be continuous values with respect to a gait progress with a start point of "0" and an end point of "1".

The stance and the swing may further be divided into a plurality of phases. For example, the stance may further be divided into an initial contact, a weight bearing, a middle stance, a terminal stance, and a pre-swing. The swing may further be divided into an initial swing, a middle swing, and a terminal swing. The stance and the swing may further be divided differently depending on an example embodiment, and are not limited thereto.

Figure 2:
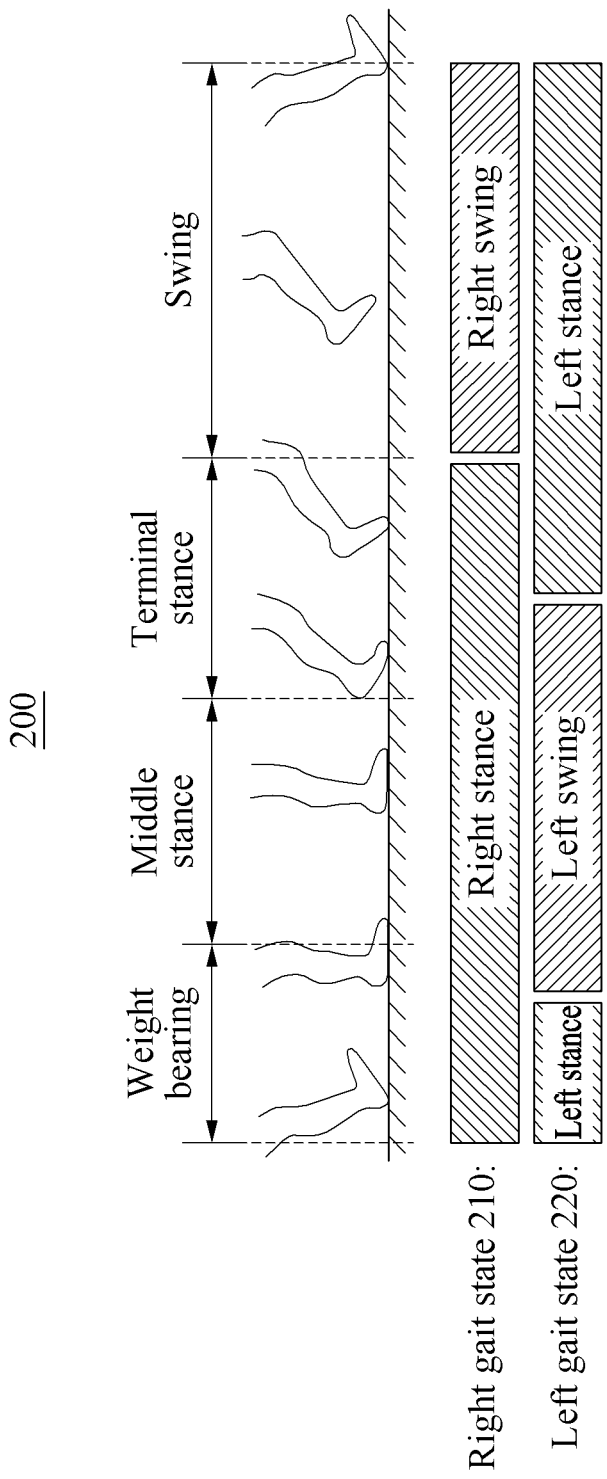
FIG. 2 illustrates a transition between gait states according to at least one example embodiment.

FIG. 2 illustrates a transition between gait states according to at least one example embodiment.

According to a general gait mechanism, gait phases of a leg may include a stance and a swing, and the stance and the swing may be performed alternately for a gait.

Referring to FIG. 2, a right gait state 210 with respect to a motion 200 of a right leg in response to a gait may include a right stance and a right swing. A stance may include a weight bearing, a middle stance, and a terminal stance, but are not limited to the disclosed and illustrated embodiments. With respect to the motion 200 of the right leg, a left gait state 220 with respect to a motion (not shown) of a left leg may include a left stance and a left swing.

A normal transition between gait states may differ depending on a gait state at a time of starting a gait. Based on an order in which events indicating starts of gait states occur, the gait states may transition in an order of a right stance, a left swing, a left stance, and a right swing. After the right swing is performed, the right stance may be performed again.

A user may feel discomfort in walking when a muscular strength of an ankle of the user is weakened due to aging or disease. For example, an end portion of a foot needs to be lifted when a leg starts swinging. If not, the swinging leg may be bumped into a floor. That is, an angle of the ankle should be adjusted as a gait phase proceeds or changes. A walking assistance apparatus may be provided to a user who has a difficulty in adjusting an angle of an ankle by himself or herself due to a weakened muscular strength of the ankle. The walking assistance apparatus may be worn around the ankle of the user, determine a gait phase of the user, and output an assistance torque corresponding to the determined gait phase. The assistance torque may be used to adjust the angle of the ankle of the user.

Further, a future gait phase as well as a gait phase of a current point in time may need to be predicted. For example, there may occur a case in which the walking assistance apparatus needs to output an assistance torque at a point in time earlier than a point in time of switching stance/swing.

Hereinafter, a method of assisting walking of a user by providing an assistance torque to an ankle of the user will be described with reference to FIGS. 3 through 17.

Figure 3:
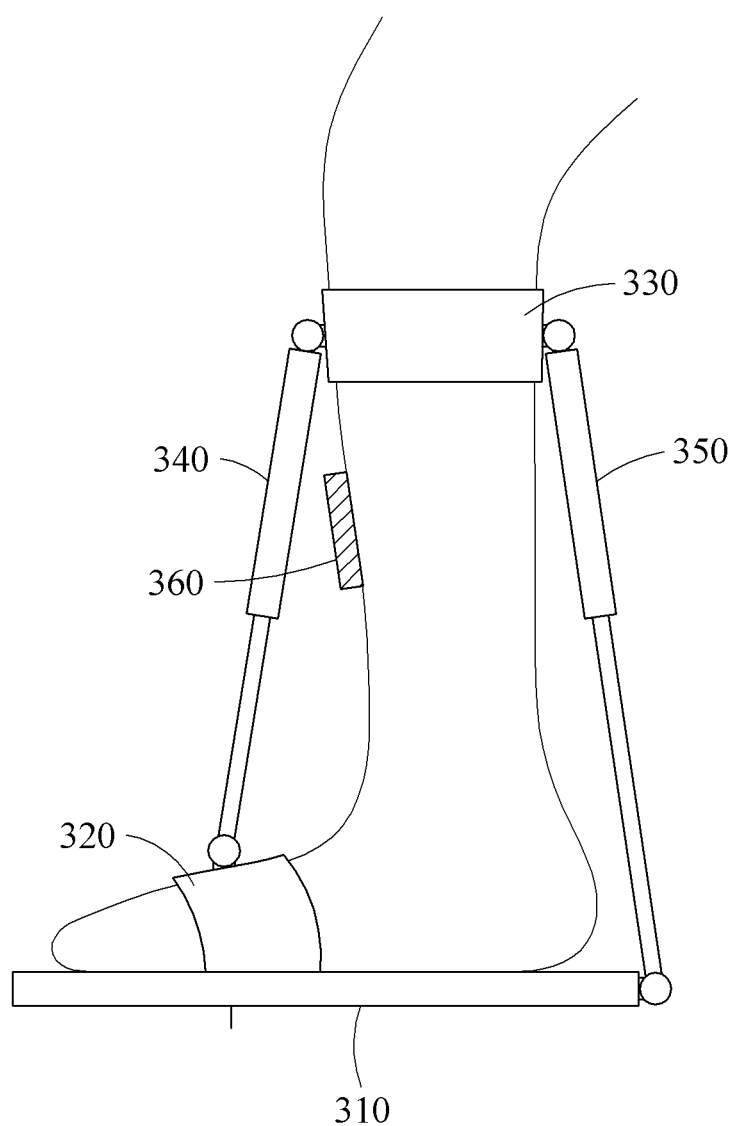
FIG. 3 illustrates a walking assistance apparatus according to at least one example embodiment.

FIG. 3 illustrates a walking assistance apparatus according to at least one example embodiment.

Referring to FIG. 3, a walking assistance apparatus 300 may include a sole frame 310, a lower fastener 320, an upper fastener 330, a first support frame 340, a second support frame 350, and an inertial measurement unit (IMU) 360. The walking assistance apparatus 300 may predict a gait phase only using the IMU 360, without using other types of sensors. For example, the walking assistance apparatus 300 may predict the gait phase based on data obtained only using the IMU 360, without using a pressure sensor disposed on a sole.

The IMU 360 may include accelerometers and gyroscopes. The IMU 360 may sense accelerations in a three-dimensional (3D) space using the accelerometers. The IMU 360 may sense rotation velocities in the 3D space using the gyroscopes. The IMU 360 may be positioned at a foot or a shank of a user.

The first support frame 340 may connect the lower fastener 320 and the upper fastener 330. The lower fastener 320 may be connected to the sole frame 310. The second support frame 350 may connect the sole frame 310 and the upper fastener 330. The upper fastener 330 may be worn on a calf or the shank of the user.

A length of the first support frame 340 and a length of the second support frame 350 may be adjusted. For example, the length of the first support frame 340 and the length of the second support frame 350 may be adjusted by a driver (not shown). The driver may adjust the length of the first support frame 340 and the length of the second support frame 350 using a mechanism.

When the length of the first support frame 340 decreases and the length of the second support frame 350 increases, the ankle of the user may be lifted. Conversely, when the length of the first support frame 340 increases and the length of the second support frame 350 decreases, the ankle of the user may extend.

Although FIG. 3 illustrates the walking assistance apparatus 300 including the first support frame 340 and the second support frame 350, the number of support frames is not limited thereto. For example, the walking assistance apparatus 300 may include only the first support frame 340, or may include at least three support frames.

Figure 4:
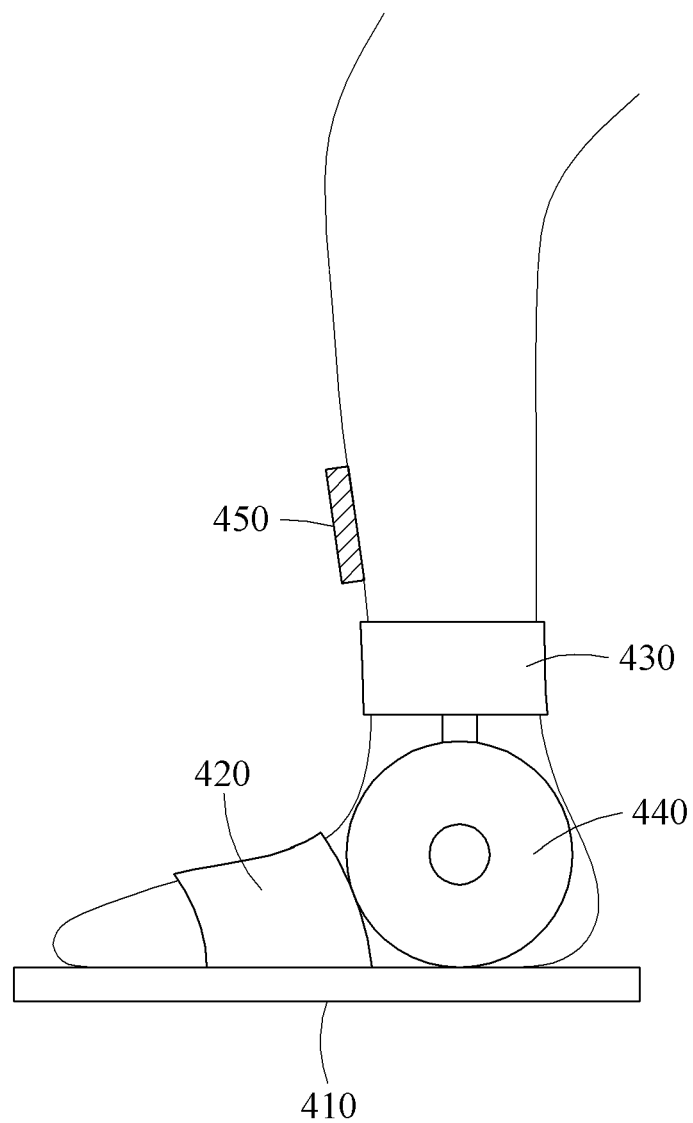
FIG. 4 illustrates a walking assistance apparatus according to at least one example embodiment.

FIG. 4 illustrates a walking assistance apparatus according to at least one example embodiment.

Referring to FIG. 4, a walking assistance apparatus 400 may include a sole frame 410, a lower fastener 420, an upper fastener 430, a motor 440, and an IMU 450.

The IMU 450 may include accelerometers and gyroscopes. The IMU 450 may sense accelerations in a 3D space using the accelerometers. The IMU 450 may sense rotation velocities in the 3D space using the gyroscopes. The IMU 450 may be positioned at a foot or a shank of a user.

The motor 440 may be connected to the lower fastener 420 and the upper fastener 430. A driver (not shown) may control the motor 440 to output a torque. When the motor 440 outputs a torque, an angle between the lower fastener 420 and the upper fastener 430 may be adjusted. For example, when the angle between the lower fastener 420 and the upper fastener 430 decreases, an ankle of the user may be lifted. Conversely, when the angle between the lower fastener 420 and the upper fastener 430 increases, the ankle of the user may extend.

Hereinafter, the method of assisting walking of a user will be described in detail with reference to FIGS. 5 through 17.

Figure 5:
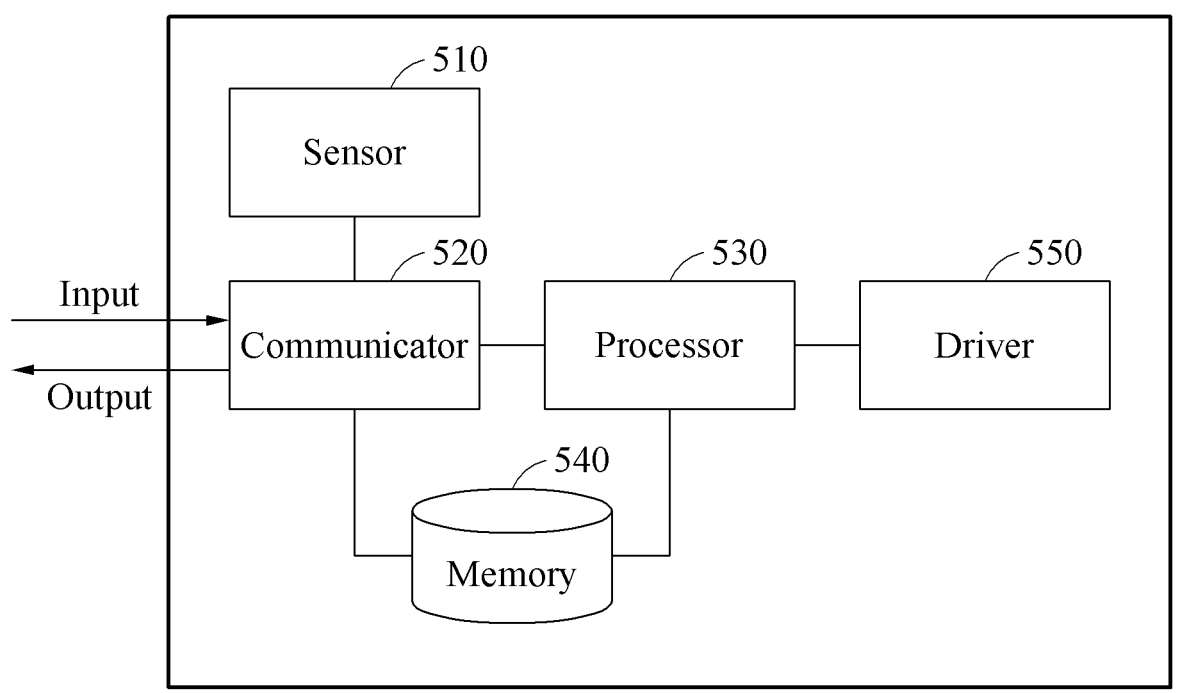
FIG. 5 illustrates a configuration of a walking assistance apparatus according to at least one example embodiment.

FIG. 5 illustrates a configuration of a walking assistance apparatus according to at least one example embodiment.

A walking assistance apparatus 500 may include at least one sensor 510, a processor 530, and a driver 550. The walking assistance apparatus 500 may further include a communicator 520, and a memory 540. The walking assistance apparatus 500 may correspond to the walking assistance apparatus 300 of FIG. 3 and the walking assistance apparatus 400 of FIG. 4 such that the walking assistance apparatus 500 also include the structural elements (e.g., fasteners, frames or motor) illustrated in FIGS. 3 or FIG. 4. The walking assistance apparatus 500 may be an ankle exoskeleton device.

The at least one sensor 510 may include an IMU. The IMU may measure accelerations and rotation velocities generated in response to a motion of the IMU. For example, the IMU may measure X-axial, Y-axial, and Z-axial accelerations and X-axial, Y-axial, and Z-axial angular velocities corresponding to a gait motion of a user.

The communicator 520 may be connected to the sensor 510, the processor 530, and the memory 540, and transmit and receive data to and from the sensor 510, the processor 530, and the memory 540. The communicator 520 may be connected to an external device and transmit and receive data to and from the external device. Hereinafter, to transmit and receive "A" may be to transmit and receive "information or data indicating A".

The communicator 520 may be implemented by a circuitry in the walking assistance apparatus 500. For example, the communicator 520 may include an internal bus and an external bus. In another example, the communicator 520 may be an element which connects the walking assistance apparatus 500 and the external device. The communicator 520 may be an interface. The communicator 520 may receive data from the external device and transmit the data to the processor 530 and the memory 540.

The processor 530 may process the data received by the communicator 520 and data stored in the memory 540. The "processor" may be a data processing device implemented by hardware including a circuit having a physical structure to perform desired operations. For example, the desired operations may include instructions or codes included in a program. For example, the hardware-implemented data processing device may include a microprocessor, a central processing unit (CPU), a processor core, a multi-core processor, a multiprocessor, an application-specific integrated circuit (ASIC), and a field programmable gate array (FPGA).

The processor 530 may execute computer-readable codes (for example, software) stored in a memory, for example, the memory 540, and instructions triggered by the processor 530.

Figure 6:
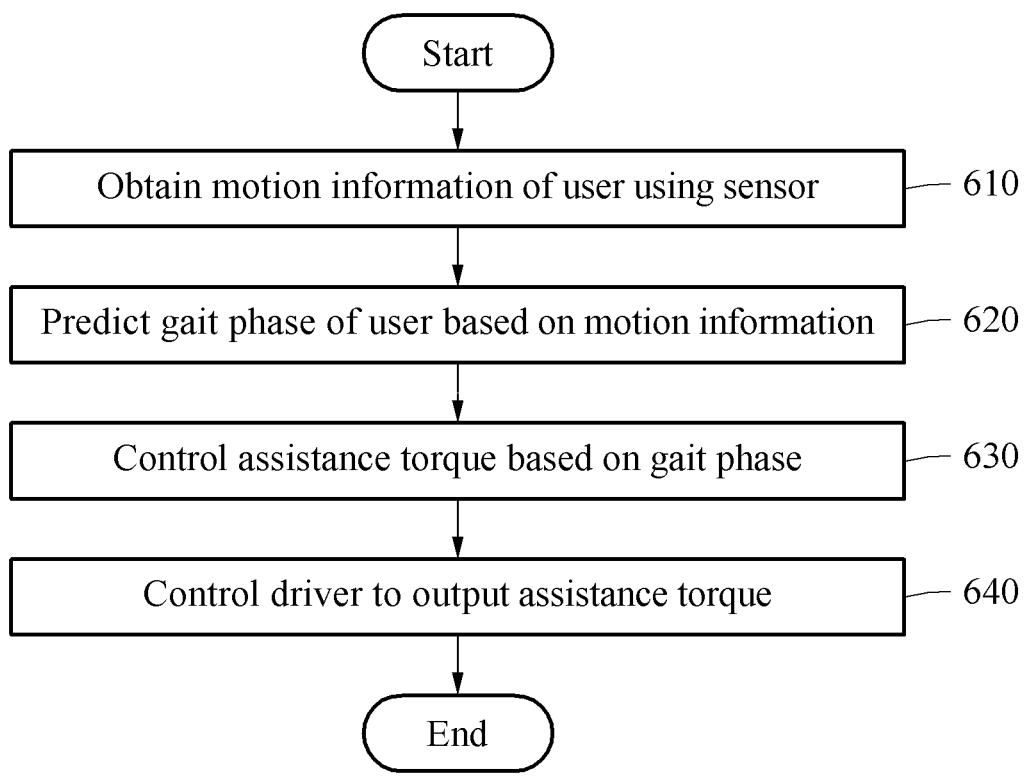
FIG. 6 is a flowchart illustrating a walking assistance method according to at least one example embodiment.

For example, the processor 530 may execute the computer-readable codes such that the processor 530 is transformed into a special purpose processor to perform the walking assistance method of FIG. 6 and/or train a gait phase regression module (PRM) based on a predicted gait phase and a determined gait phase. Therefore, the processor 530 may improve the functioning of the walking assistance apparatus itself by increasing the accuracy of predicting continuous motions of the gait associated with a boundary of a gait cycle.

The memory 540 may store the data received by the communicator 520 and the data processed by the processor 530. For example, the memory 540 may store the program. The stored program may be a set of syntaxes coded to assist walking of a user and executable by the processor 530.

The memory 540 may include at least one volatile memory, non-volatile memory, random access memory (RAM), flash memory, hard disk drive, and optical disk drive.

The memory 540 may store a command set, for example, software, to operate the walking assistance apparatus 500. The command set to operate the walking assistance apparatus 500 may be executed by the processor 530.

The driver 550 may include mechanisms to adjust an angle of an ankle of the user. For example, the driver 550 may include a motor, and a torque output by the motor may be used to adjust the angle of the ankle. In another example, the driver 550 may include a power converting device which adjusts a length of a support frame. The power converting device may convert a rotational motion generated by the driver 550 into a rectilinear motion.

The walking assistance apparatus 500 may include a powered orthosis or robotic orthosis which assists a physiological function like an ankle exoskeleton device, and a robotic prosthesis which replaces a missing body part.

The sensor 510, the communicator 520, the processor 530, the memory 540, and the driver 550 will be described further with reference to FIGS. 6 through 17.

FIG. 6 is a flowchart illustrating a walking assistance method according to at least one example embodiment.

Operations 610 through 630 may be performed by the walking assistance apparatus 500 of FIG. 5. The walking assistance apparatus 500 may be implemented by one or more hardware modules, one or more software modules, or various combinations thereof.

In operation 610, the walking assistance apparatus 500 may receive or obtain information related to a motion of a user from a sensor. For example, the sensor 510 may include an IMU. The IMU may measure acceleration information, rotation velocity information, or a combination thereof in relation to a motion of a user. The rotation velocity information may be information related to an angular velocity.

In operation 620, the walking assistance apparatus 500 may predict a gait phase of the user based on the received information related to the motion of the user. The gait phase may include information indicating a gait process in a predefined period corresponding to a gait cycle. The gait cycle may be a period including repetitive patterns occurring during walking and include, for example, the right stance RSt and the right swing RSw of FIG. 1. The gait cycle may be defined separately for a right leg and a left leg. Referring to FIG. 2, a gait cycle for the right leg and a gait cycle for the left leg may differ from each other.

The predefined period may be a period defined repeatedly for a gait, and may include, for example, a period from a start point of a stance period to a start point of a subsequent stance period, or a period from a start point of a swing period to a start point of a subsequent swing period. In another example, the predefined period may include a period from a predetermined point in time instead of a start point to a corresponding point in time of a subsequent cycle.

For example, the walking assistance apparatus 500 may predict a gait progress in a gait cycle based on motion information measured by the sensor. An example of predicting a gait phase of a user will be described in detail with reference to FIGS. 7A through 8.

In operation 630, the walking assistance apparatus 500 may control an assistance torque based on the predicted gait phase. For example, the walking assistance apparatus 500 may calculate an assistance torque corresponding to the gait progress. A trajectory of the assistance torque with respect to the gait phase may be preset corresponding to the gait progress. The walking assistance apparatus 500 may determine a point in time at which the assistance torque is to be applied based on the predicted gait phase, and determine a magnitude of the assistance torque corresponding to the determined point in time.

The walking assistance apparatus 500 may further perform operation 640. In operation 640, the walking assistance apparatus 500 may control the driver 550 to output the assistance torque. An example of controlling the driver will be described further with reference to FIG. 10.

Figure 7A:
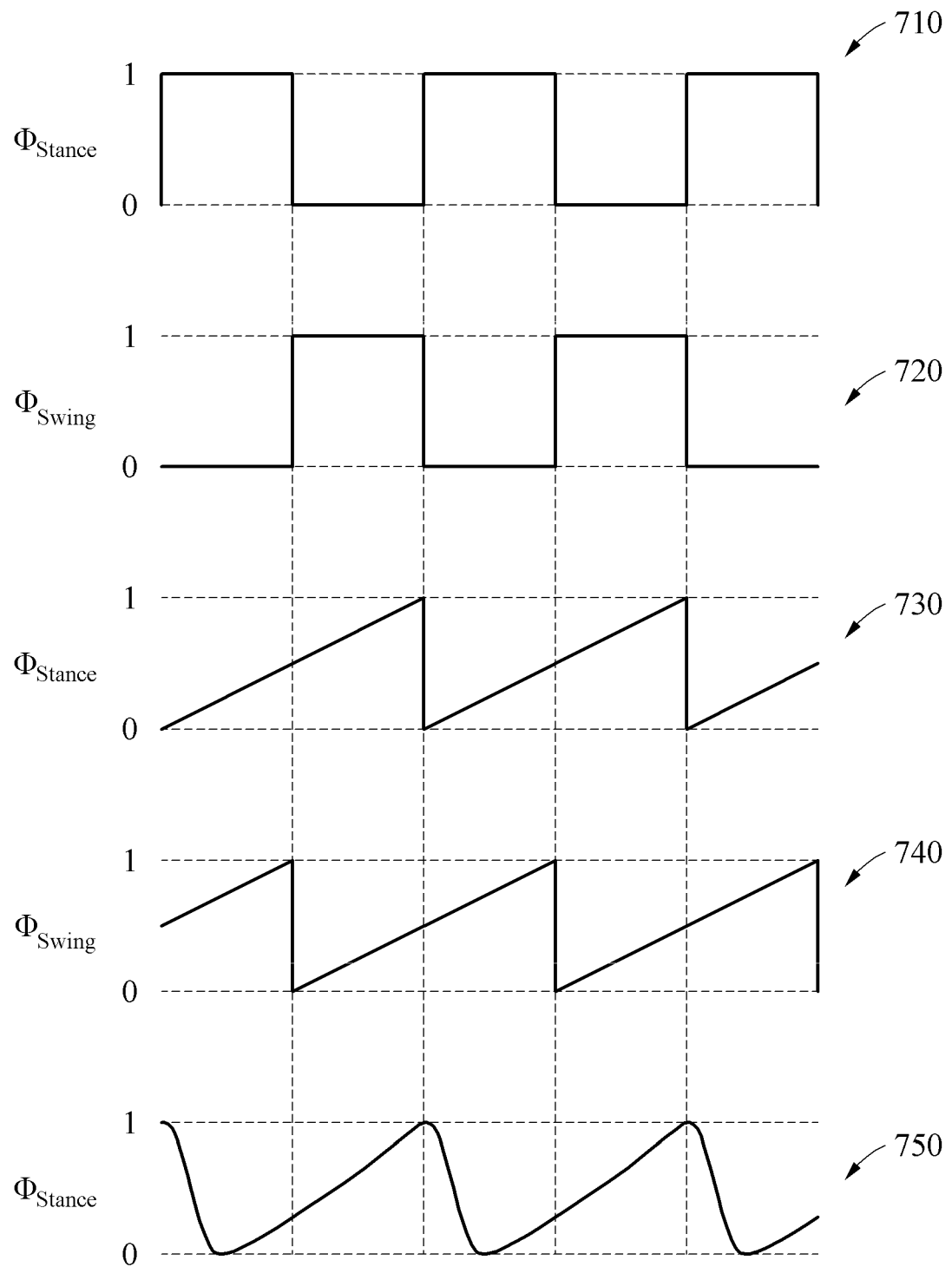
FIG. 7A illustrates graphs to describe forms of gait phases according to at least one example embodiment.

FIG. 7A illustrates graphs to describe forms of gait phases according to at least one example embodiment.

Referring to FIG. 7A, a gait phase related to motion information of a user may be represented separately based on a stance and a swing. For example, a graph 710, 720 may be a graph showing discontinuous data classified into a stance and a swing. In the graph 710 related to a gait phase with respect to a stance of a leg, a stance state may be represented with a value of "1", and a swing state may be represented with a value of "0". In the graph 720 related to a gait phase with respect to a swing of a leg, a swing state may be represented with a value of "1", and a stance state may be represented with a value of "0".

The gait phase may be represented with continuous data related to a gait progress in a predefined period corresponding to a gait cycle. For example, referring to a graph 730, the gait phase may be mapped to "0" at a first point in time at which a stance is started, and the gait phase may be mapped to "1" at a second point in time at which the stance is restarted. The gait phase between the first point in time and the second point in time may be mapped to continuous values between "0" and "1" related to the gait progress. Referring to a graph 740, the gait phase with respect to the swing may be mapped in a manner substantially the same as the manner described through the graph 730.

The graph 730, 740 is a continuous gait phase graph, and the graph 710, 720 is a discontinuous gait phase graph. Thus, when the graph 730, 740 is used, a more precise control may be enabled than when the graph 710, 720 is used. For example, only two states of "0" and "1" may be determined according to the graph 710, 720, whereas a point in time corresponding to a value between "0" and "1", for example, "0.6" of the gait phase, may be determined according to the graph 730, 740.

The walking assistance apparatus 500 may predict continuous gait phases, for example, the graph 730, 740, corresponding to information related to the motion of the user, based on the information related to the motion of the user received from the sensor.

The walking assistance apparatus 500 may use a gait phase regression module (PRM) to predict the continuous gait phases corresponding to the information related to the motion of the user. The gait PRM may include a pre-trained neural network. In this example, the walking assistance apparatus 500 may input the information related to the motion of the user into the pre-trained neural network. The neural network may include an input layer, a hidden layer, and an output layer. The input layer may have a structure suitable for receiving the information related to the motion of the user collected by the sensor, and the output layer may have a structure suitable for outputting data indicating the continuous gait phases.

An operation of training a neural network with respect to a gait phase may be performed by the walking assistance apparatus 500. For example, the walking assistance apparatus 500 may receive, from a first sensor, first information related to a motion of a user wearing the walking assistance apparatus. The first sensor may include an IMU. The walking assistance apparatus 500 may receive, from a second sensor, second information related to the motion of the user. The second sensor may include a contact sensor. The contact sensor may sense whether a foot of the user contacts the ground. The walking assistance apparatus 500 may determine a gait phase corresponding to the first information based on the second information. The determined gait phase may be utilized as a label or a ground truth to train the neural network. The walking assistance apparatus 500 may predict the gait phase by applying the first information to the gait PRM. The walking assistance apparatus 500 may train the gait PRM based on the predicted gait phase and the determined gait phase. For example, the walking assistance apparatus 500 may train parameters of the neural network so as to minimize a difference between the predicted gait phase and the determined gait phase.

An operation of training a neural network with respect to a gait phase may be performed by a separate server device. The server device may use training data provided in advance or training data collected from at least one user. The server device may also use training data generated by a simulation.

The neural network may be pre-trained to predict a gait phase corresponding to acceleration information and rotation velocity information according to various gait patterns. For example, the neural network may be pre-trained with a gait phase corresponding to acceleration information and rotation velocity information according to various gait patterns such as level walking, level running, slope walking, and slop running of a normal user. Further, the neural network may be pre-trained with a gait phase corresponding to acceleration information and rotation velocity information according to various gait patterns such as level walking, level running, slope walking, and slop running of a user having a difficulty in normal walking.

The neural network may be trained to predict gait phases, for example, the graph 730, 740, having continuous values corresponding to a gait progress. In an example in which the neural network is trained to map 3D acceleration and 3D angular velocity values of a user directly to a gait phase, a smoothed result like a graph 750, rather than the graph 730, 740, may be predicted. For example, a gait of a user includes continuous motions having a gait cycle, whereas the gait phases of the graph 730, 740 are discontinuous on a boundary of the gait cycle. Thus, the neural network may not accurately predict the continuous motions of the gait on the boundary of the gait cycle. Further, in an example in which a gait phase is predicted using the smoothed graph like the graph 750, a precise control may be relatively difficult when compared to an example of an unsmoothed graph like the graph 730, 740. A method of training a neural network to obtain an unsmoothed graph like the graph 730, 740 will be described further below.

Figure 7B:
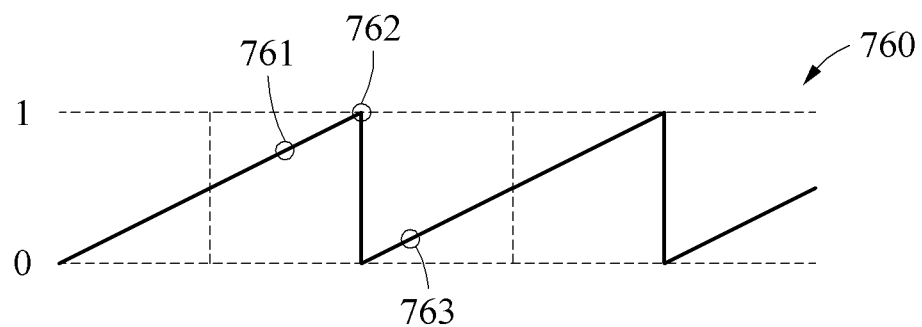
FIG. 7B illustrates output data of a neural network according to at least one example embodiment.
Figure 7B:
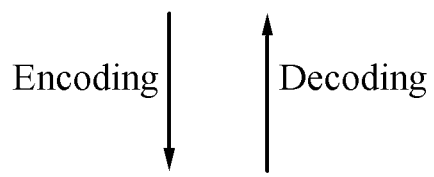
Figure 7B:
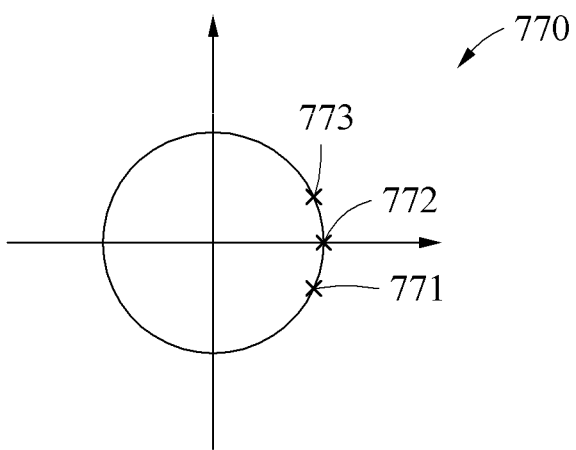

FIG. 7B illustrates output data of a neural network according to at least one example embodiment. Referring to FIG. 7B, a gait phase 760 having continuous values in a gait cycle may be encoded into a circle 770 having a continuity on a boundary of the gait cycle to train a neural network. For example, a first gait phase 761 belonging to a second half of the gait cycle may be mapped to a vertex 771 on the circle 770, a second gait phase 762 belonging to the boundary of the gait cycle may be mapped to a vertex 772 on the circle 770, and a third gait phase 763 belonging to a first half of a subsequent gait cycle may be mapped to a vertex 773 on the circle 770.

When six-dimensional (6D) information related to measured accelerations and angular velocities is input, the neural network may be pre-trained to output a two-dimensional (2D) vector of cosine and sine values indicating a gait phase with respect to a stance, a 2D vector of cosine and sine values indicating a gait phase with respect to a swing, or a four-dimensional (4D) vector combining the same. The 2D vector may correspond to coordinates indicating a vertex on the circle 770.

For example, the neural network may be trained to output y1=cos 0 and y2=sin 0 based on 6D information related to accelerations and angular velocities measured at a point in time at which a stance is started. The neural network may be trained to output y1=cos 2π and y2=sin 2π based on 6D information related to accelerations and angular velocities measured at a point in time immediately before the stance is started. The neural network may be trained to output y1=cos 1.2π and y2=sin 1.2π based on 6D information related to accelerations and angular velocities measured at a point in time at which a swing is started.

The neural network may be trained to output data encoded to have a continuity on the boundary of the gait cycle, rather than being trained to output the gait phase 760 directly. Thus, a result predicted by the neural network may be inhibited (or, alternatively, prevented) from being smoothed on the boundary of the gait cycle.

In further detail, in an example in which the neural network is trained to map the measured accelerations and angular velocities directly to a gait phase, a smoothed gait phase may be predicted on the boundary of the gait cycle since a gait phase at a point in time immediately before a stance is started and a gait phase at a point in time at which the stance is started are discontinuous.

Conversely, in an example in which the neural network is trained such that the measured accelerations and angular velocities correspond to trigonometrical function data corresponding to the gait phase, a value output at a point in time immediately before the stance is started and a value output at a point in time at which the stance is started are maintained to be continuous by a periodicity of a trigonometrical function, whereby prediction of a smoothed gait phase on the boundary of the gait cycle may be inhibited (or, alternatively, prevented).

In an inference process after training is completed, when the encoded data is output from the neural network, the walking assistance apparatus 500 may obtain the gait phase by decoding the corresponding data. Operations of the inference process will be described later with reference to FIGS. 8 through 11.

Although not shown in the drawings, another figure may be used for encoding, instead of a circle. For example, the other figure may include a polygon, and an untwisted closed curve. In this example, the data may include information indicating a vertex corresponding to a gait phase, among a plurality of vertices included in a perimeter of a figure corresponding to a gait cycle. Further, the data may have a continuity on the boundary of the gait cycle. For example, on a boundary between a current gait cycle to a subsequent gait cycle, a figure, for example, a polygon, may be determined such that data may change by a minimum unit representing a gait phase.

Figure 8:
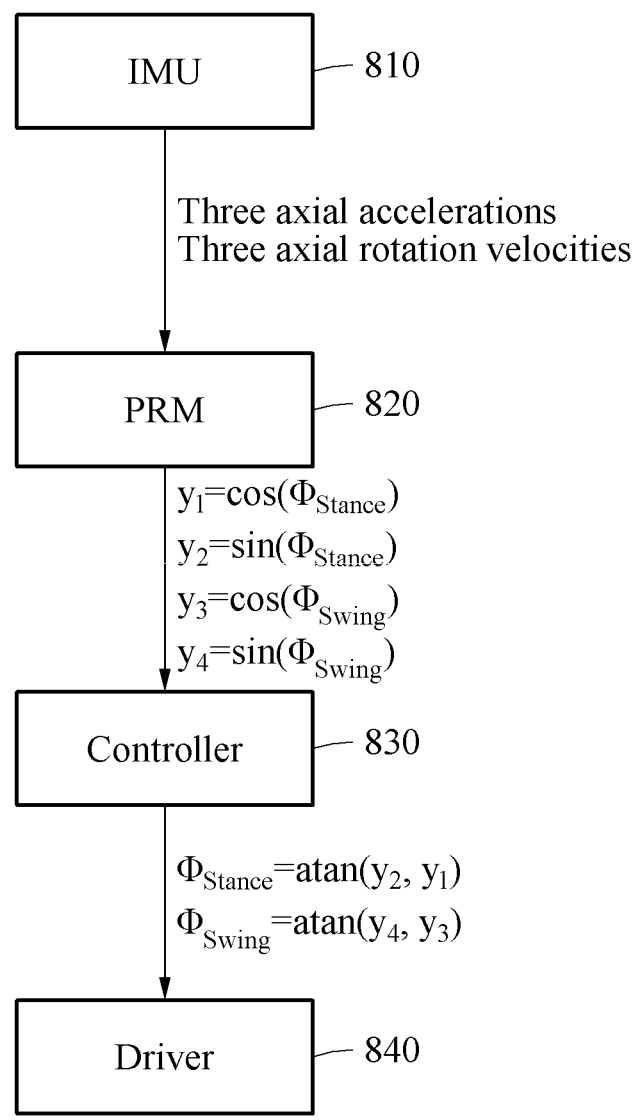
FIG. 8 illustrates a walking assistance apparatus and parameters according to at least one example embodiment.

FIG. 8 illustrates a walking assistance apparatus and parameters according to at least one example embodiment.

Referring to FIG. 8, an IMU 810 may be attached to a foot or a shank of a user to measure a motion of the user and obtain 6D information related to accelerations and angular velocities. For example, the IMU 810 may measure X-axial, Y-axial, and Z-axial accelerations, and X-axial, Y-axial, and Z-axial angular velocities corresponding to a gait motion of the user.

The 6D information related to the measured accelerations and angular velocities may be input into a gait phase regression module (PRM) 820. The gait PRM 820 may be a module trained by machine learning, and may output a trigonometrical function value of a gait phase with respect to a stance and a gait phase with respect to a swing. Trigonometrical function data with respect to the gait phase may be referred to as first data. The machine learning may include a recurrent neural network (RNN). The trigonometrical function may include a cosine function and a sine function. For example, the gait PRM 820 may output cosine values and sine values of the gait phase with respect to the stance and the gait phase with respect to the swing as a 4D vector.

The gait PRM 820 may determine the gait phase with respect to the stance and the gait phase with respect to the swing using the 4D vector corresponding to the cosine values and the sine values of the gait phase with respect to the stance and the gait phase with respect to the swing. For example, the gait PRM 820 may obtain the gait phase with respect to the stance and the gait phase with respect to the swing by performing an arctan operation on the determined cosine and sine values. The gait phase obtained by the gait PRM 820 may be an unsmoothed graph like the graph 730, 740.

A controller 830 may control a driver 840 to output an assistance force to assist walking of a user. A predetermined assistance torque may be controlled based on a gait phase at a desired point in time. For example, the controller 830 may output a control signal to control the driver 840 to generate the torque. The controller 830 may include a communicator, a processor, and a memory.

The driver 840 may generate the torque based on the control signal output from the controller 830. The driver 840 may provide a driving force to an ankle of the user. For example, the driver 840 may control the ankle such that a center of gravity of the user may be formed at a front side of a sole. The driver 840 may include a motor which generates a rotational torque.

Figure 9:
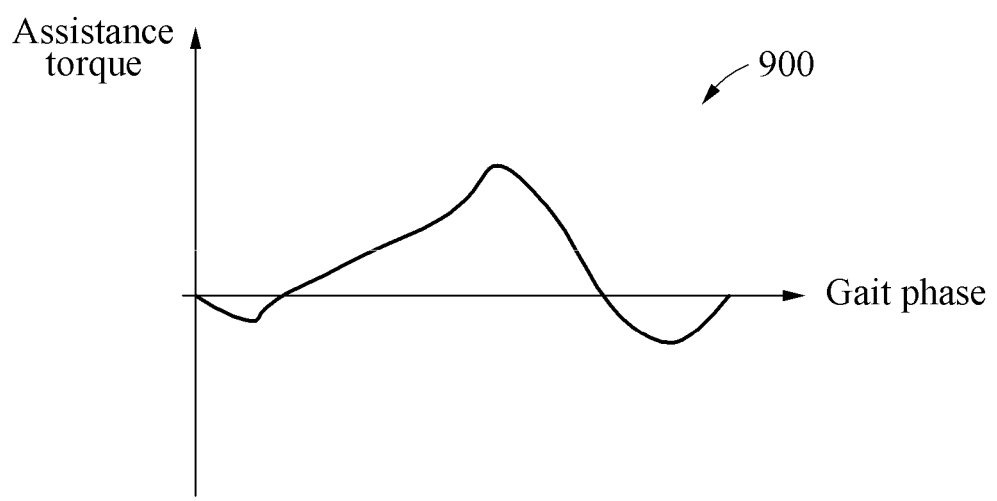
FIG. 9 is a graph illustrating an assistance torque predetermined based on a gait phase according to at least one example embodiment.

FIG. 9 is a graph illustrating an assistance torque predetermined based on a gait phase according to at least one example embodiment.

Referring to a graph 900 of FIG. 9, an assistance torque needed by a user may be predetermined based on a gait phase. The walking assistance apparatus 500 may calculate an assistance torque corresponding to a stance or a swing. A point in time at which the assistance torque is to be applied and a magnitude of the assistance torque corresponding to the point in time may be determined based on the predicted gait phase. A trajectory of the assistance torque with respect to the gait phase may be preset. For example, the trajectory of the assistance torque may be preset as shown in a graph 900. In the graph 900, an axis x may denote the point in time at which the assistance torque is to be applied, and an axis y may denote the magnitude of the assistance torque corresponding to the point in time. An angle of the ankle of the user may be adjusted by the assistance torque. The walking assistance apparatus 500 may control a driver to output an assistance torque. An example of controlling the driver will be described in detail with reference to FIG. 10.

Figure 10:
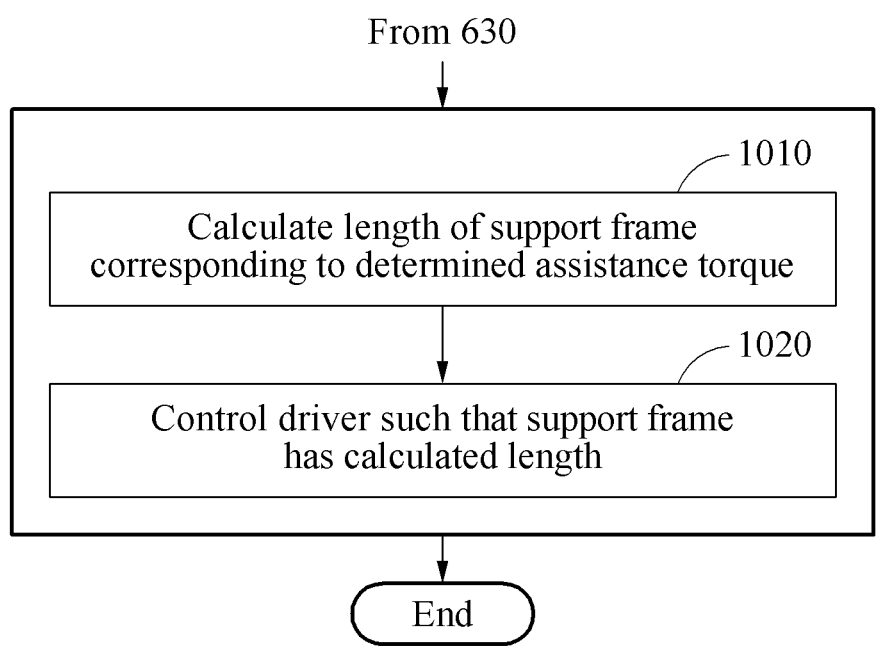
FIG. 10 is a flowchart illustrating an example of controlling a driver by adjusting a length of a support frame according to at least one example embodiment.

FIG. 10 is a flowchart illustrating an example of controlling a driver by adjusting a length of a support frame according to at least one example embodiment.

Operation 640 of FIG. 6 may include operations 1010 and 1020. An embodiment using operations 1010 and 1020 may correspond to the walking assistance apparatus 300 of FIG. 3.

In operation 1010, the walking assistance apparatus 500 may calculate a length of a support frame corresponding to the determined assistance torque. For example, the length of the support frame corresponding to the assistance torque may be stored in advance.

In operation 1020, the walking assistance apparatus 500 may control the driver 550 such that the support frame may have the calculated length. For example, the driver 550 may adjust the length of the support frame using a power converting device. The power converting device may be a device which converts a rotational motion of a motor into a rectilinear motion.

Figure 11:
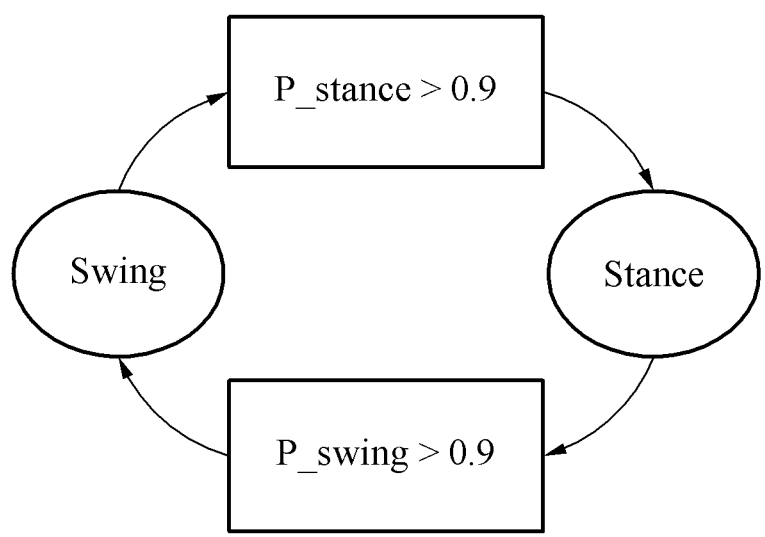
FIG. 11 illustrates a walking assistance method which distinguishes between two states of stance and swing according to at least one example embodiment.

FIG. 11 illustrates a walking assistance method which distinguishes between two states of stance and swing according to at least one example embodiment.

Referring to FIG. 11, when 6D information related to measured accelerations and angular velocities is input into a classifier provided in advance, the classifier may output a probability of a stance P_stance and a probability of a swing P_swing.

A walking assistance apparatus may switch an inner state as expressed by Equation 1.

If (current state==Stance AND P_swing>alpha) Then
 current state←Swing

If (current state==Swing AND P_stance>alpha) Then
 current state←Stance     [Equation 1]

In Equation 1, alpha denotes a predetermined threshold, and may be determined to be, for example, a value between "0" and "1". As alpha is relatively close to "1", the stance/swing states may switch conservatively. In an example in which alpha=0.9 and the inner state is the stance state, the inner state may switch from the stance state to the swing state only when the probability of the swing output from the classifier is greater than or equal to 90%.

Figure 12:
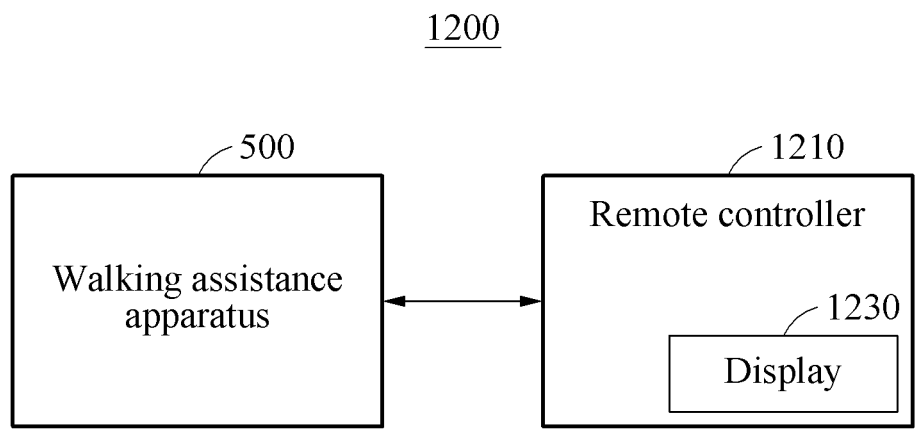
FIG. 12 is a block diagram illustrating a walking assistance system according to at least one example embodiment.

FIG. 12 is a block diagram illustrating a walking assistance system according to at least one example embodiment.

Referring to FIG. 12, a walking assistance system 1200, also referred to as a gait assist system or a walking assist system, may include the walking assistance apparatus 500, and a remote controller 1210.

The remote controller 1210 may control an overall operation of the walking assistance apparatus 500 in response to a user input. For example, the remote controller 1210 may initiate or terminate the operation of the walking assistance apparatus 500. Further, the remote controller 1210 may control an assistance torque output from the walking assistance apparatus 500 to control a walking assistance for the user.

The remote controller 1210 may include a display 1230. The display 1230 may be implemented by a touch screen, a liquid crystal display (LCD), a thin film transistor-LCD (TFT-LCD), a light emitting diode (LED) display, an organic LED (OLED) display, an active matrix OLED (AMOLED) display, or a flexible display.

The remote controller 1210 may provide a user with a menu and/or a user interface (UI) corresponding to a function to control the walking assistance apparatus 500 through the display 1230.

The display 1230 may display an operating state of the walking assistance apparatus 500 to the user based on the control of the remote controller 1210.

Hereinafter, a hip-type walking assistance apparatus which may be additionally combined with the walking assistance apparatus 500 described with reference to FIGS. 5 through 12 will be described with reference to FIGS. 13 and 14. The hip-type walking assistance apparatus may be an apparatus which provides a walking assistance force to a hip joint of a user. The walking assistance apparatus 500 may be connected to the hip-type walking assistance apparatus via wired communication or wireless communication. The walking assistance apparatus 500 and the hip-type walking assistance apparatus may provide the user with an assistance torque with respect to a gait phase determined for a motion of the user. For example, the walking assistance apparatus 500 may provide the assistance torque to an ankle joint of the user, and the hip-type walking assistance apparatus may provide the assistance torque to the hip joint of the user.

Overview of Hip-Type Walking Assistance Apparatus

Figure 13:
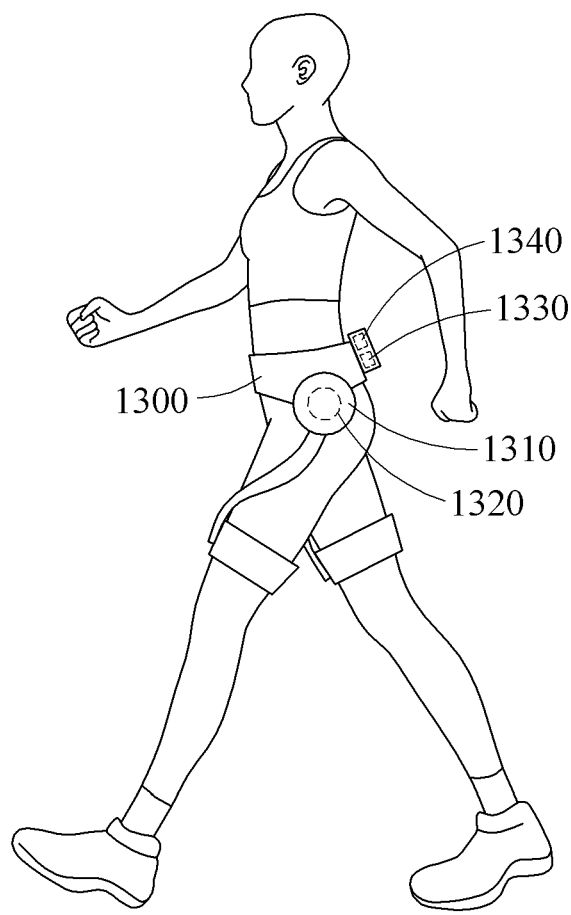
FIGS. 13 and 14 illustrate a hip-type walking assistance apparatus according to at least one example embodiment.
Figure 14:
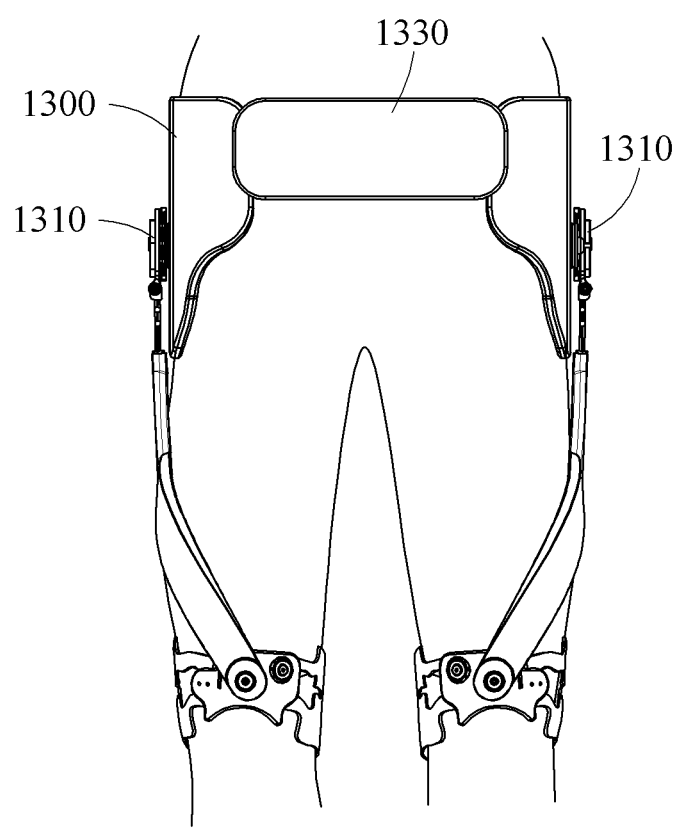

FIGS. 13 and 14 illustrate a hip-type walking assistance apparatus according to at least one example embodiment.

Referring to FIG. 13, a hip-type walking assistance apparatus 1300 may be attached to a user and assist walking of the user. The walking assistance apparatus 1300 may be a wearable device.

Example embodiments described with reference to FIGS. 13 and 14 may be applied to the hip-type walking assistance apparatus. However, the example embodiments are not limited thereto, and may be applied to any device which assists walking of a user.

The hip-type walking assistance apparatus 1300 may include a driver 1310, a sensor 1320, an IMU 1330, and a controller 1340.

The driver 1310 may provide a driving force to a hip joint of the user. For example, the driver 1310 may be positioned on a right hip and/or a left hip of the user. The driver 1310 may include a motor which generates a rotational torque.

The sensor 1320 may measure an angle of the hip joint of the user during walking. Information related to the angle of the hip joint sensed by the sensor 1320 may include an angle of a right hip joint, an angle of a left hip joint, a difference between the angles of both hip joints, and movement directions of the hip joints. For example, the sensor 1320 may be positioned in the driver 1310.

The sensor 1320 may include a potentiometer. The potentiometer may sense right (R)-axial and left (L)-axial joint angles and R-axial and L-axial joint angular velocities corresponding to a gait motion of the user.

The IMU 1330 may measure acceleration information and pose information during walking. For example, the IMU 1330 may sense X-axial, Y-axial, and Z-axial accelerations and X-axial, Y-axial, and Z-axial angular velocities corresponding to the gait motion of the user.

The hip-type walking assistance apparatus 1300 may detect a point at which a foot of the user lands based on the acceleration information measured by the IMU 1330.

The hip-type walking assistance apparatus 1300 may include other sensors which sense a change in biosignal or quantity of motion of the user in response to the gait motion, in addition to the sensor 1320 and the IMU 1330 described above. The other sensors may include, for example, an electromyogram (EMG) sensor and an electroencephalogram (EEG) sensor.

The controller 1340 may control the driver 1310 to output an assistance force to assist walking of the user. For example, the hip-type walking assistance apparatus 1300 may include two drivers 1310 for the left hip and the right hip. The controller 1340 may output a control signal to control the driver 1310 to generate a torque. The controller 1340 may include a communicator, a processor, and a memory.

The driver 1310 may generate the torque based on the control signal output from the controller 1340. The hip-type walking assistance apparatus 1300 may include the driver 1310 for the right leg and the driver 1310 for the left leg. For example, the controller 1340 may be designed to control one of the drivers 1310. In an example in which the controller 1340 controls only one of the drivers 1310, there may be a plurality of controllers 1340. In another example, the controller 1340 may be designed to control all the drivers 1310.

Unlike the hip-type walking assistance apparatus 1300 described with reference to FIGS. 13 and 14, the walking assistance apparatus 500 may be included in a full body-type walking assistance apparatus 1 which will be described with reference to FIGS. 15 through 17. The full body-type walking assistance apparatus 1 may be a device which provides a walking assistance force to each of a hip joint, a knee joint, and an ankle joint of a user.

Overview of Full Body-Type Walking Assistance Apparatus

Figure 15:
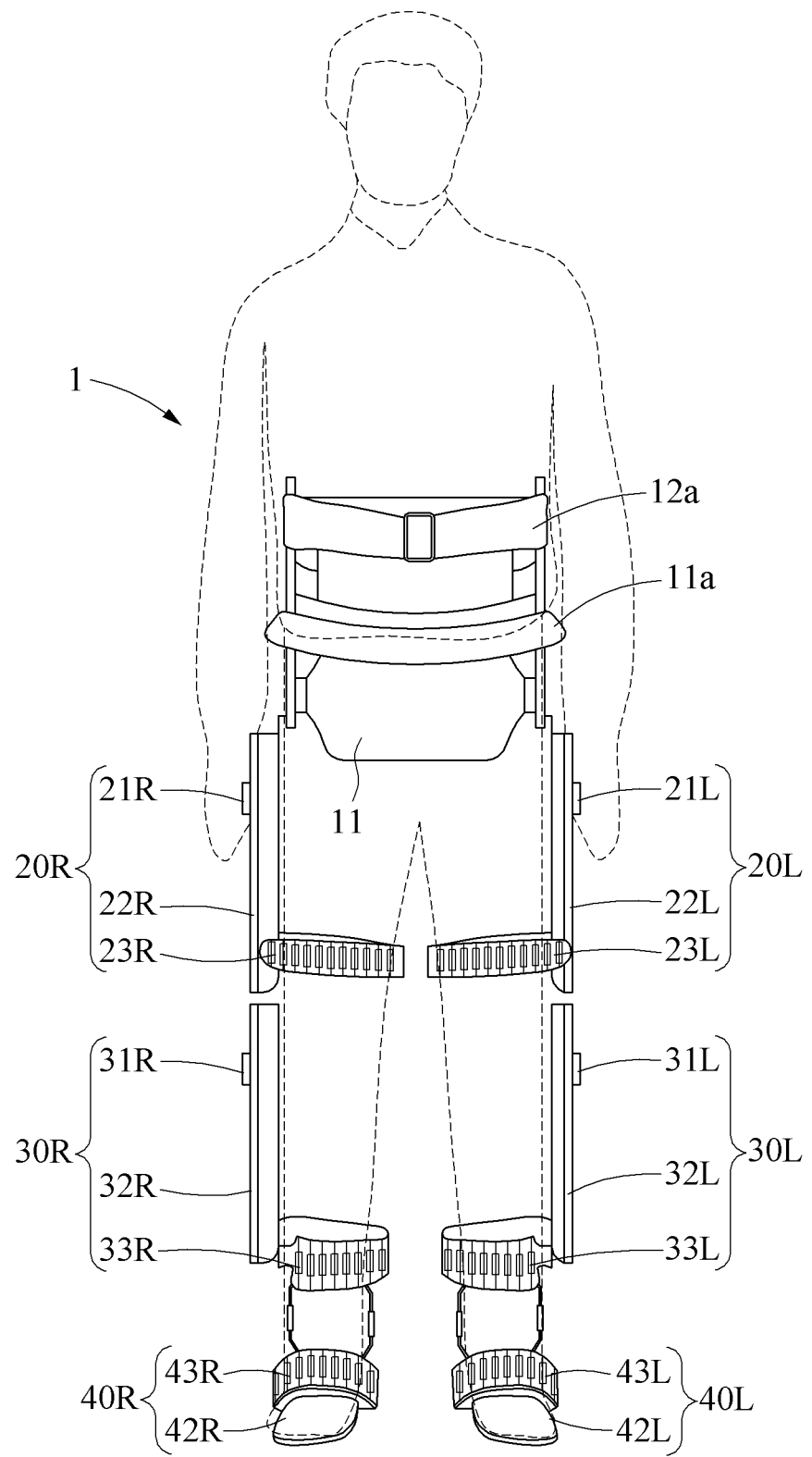
FIGS. 15 through 17 illustrate a full body-type walking assistance apparatus according to at least one example embodiment.
Figure 16:
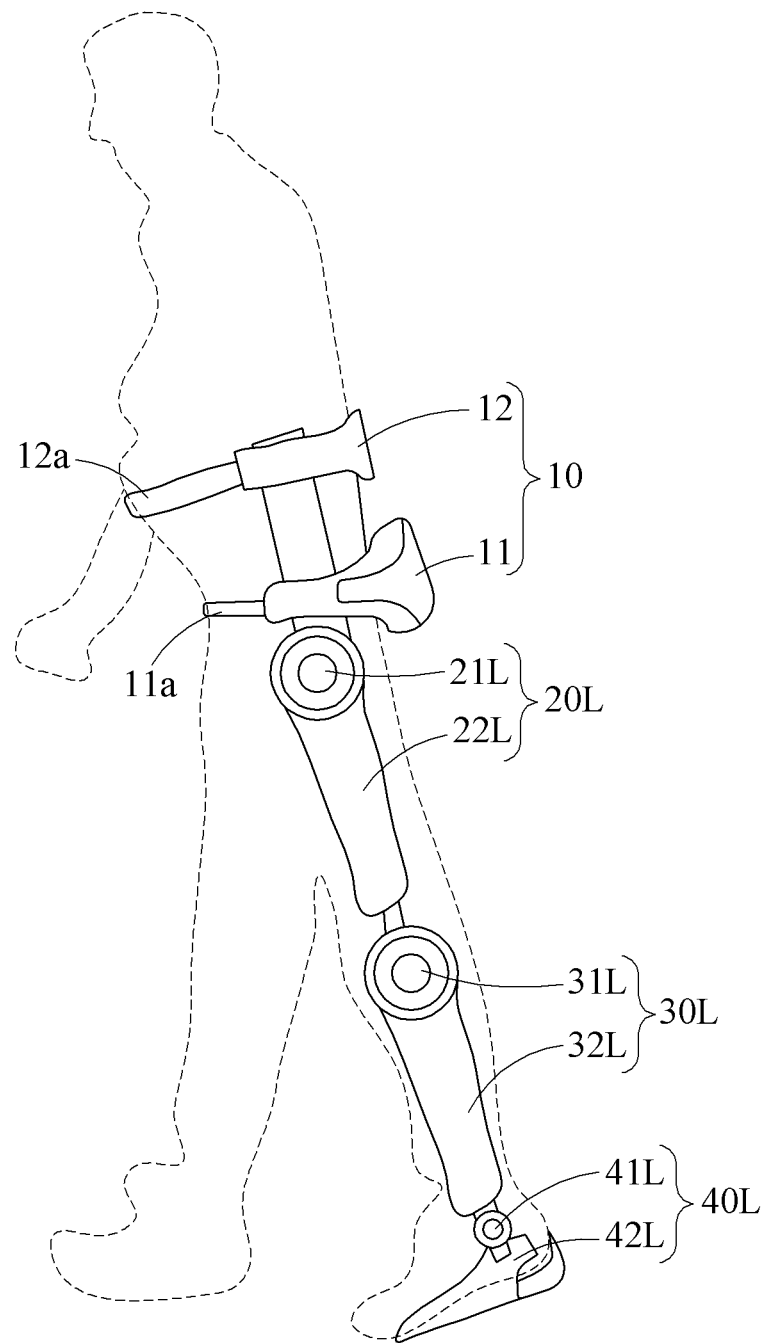
Figure 17:
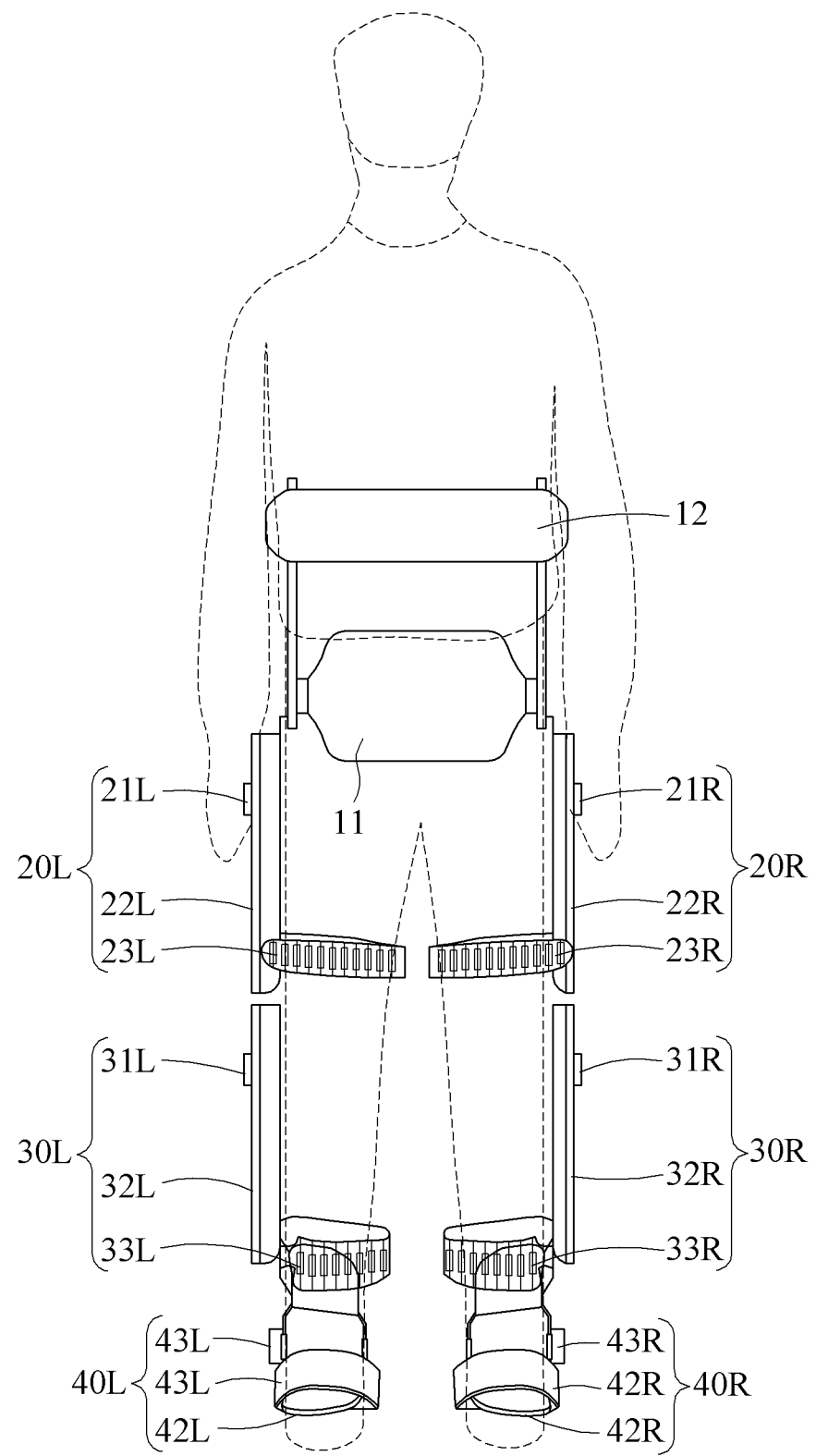

FIGS. 15 through 17 illustrate a full body-type walking assistance apparatus according to at least one example embodiment. FIG. 15 is a front view of the full body-type walking assistance apparatus 1, FIG. 16 is a side view of the full body-type walking assistance apparatus 1, and FIG. 17 is a rear view of the full body-type walking assistance apparatus 1.

The full body-type walking assistance apparatus 1 may include the driver 1310, the sensor 1320, the IMU 1330, and the controller 1340 described above.

As shown in FIGS. 15 through 17, the full body-type walking assistance apparatus 1 may have an exoskeleton structure such that the full body-type walking assistance apparatus 1 may be worn on a left leg and a right leg of a user. The user may perform motions such as an extension, a flexion, an adduction, and an abduction while wearing the walking assistance apparatus 1. The extension may be a motion to extend a joint, and the flexion may be a motion to flex the joint. The adduction may be a motion to move a leg close to a central axis of a body. The abduction may be a motion to stretch the leg away from the central axis of the body.

Referring to FIGS. 14 through 17, the full body-type walking assistance apparatus 1 may include a main body 10, and mechanisms 20, 30, and 40.

The main body 10 may include a housing 11. Various components may be provided in the housing 11. The components provided in the housing 11 may include, for example, a CPU, a printed circuit board (PCB), various types of storage devices, and a power source. The main body 10 may include the controller 1340 described above. The controller 1340 may include a CPU and a PCB.

The CPU may be a microprocessor. The microprocessor may include an arithmetic logical operator, a register, a program counter, a command decoder, and/or a control circuit on a silicon chip. The CPU may select a control mode suitable for a gait environment and generate a control signal to control operations of the mechanisms 20, 30, and 40 based on the selected control mode.

The PCB may be a board on which a predetermined circuit is printed. A CPU and/or various storage devices may be provided on the PCB. The PCB may be fixed to an inner side surface of the housing 11.

Various types of storage devices may be provided in the housing 11. The storage devices may be magnetic disk storage devices to store data by magnetizing a surface of a magnetic disk, and semiconductor memory devices to store data using various types of memory semiconductors.

The power source provided in the housing 11 may supply a driving power to the various components provided in the housing 11, or the mechanisms 20, 30, and 40.

The main body 10 may further include a waist support 12 to support a waist of the user. The waist support 12 may have a shape of a curved plane so as to support the waist of the user.

The main body 10 may further include a fixer 11a to fix the housing 11 to a hip of the user, and a fixer 12a to fix the waist support 12 to the waist of the user. The fixer 11a, 12a may be implemented by one of a band, a belt, and a strap having elasticity.

The main body 10 may include the IMU 1330 described above. For example, the IMU 1330 may be provided outside or inside the housing 11. The IMU 1330 may be provided on the PCB in the housing 11. The IMU 1330 may measure accelerations and angular velocities.

The mechanisms 20, 30, and 40 may include a first structure 20R, 20L, a second structure 30R, 30L, and a third structure 40R, 40L, respectively, as shown in FIGS. 15 through 17.

The first structure 20R, 20L may assist motions of a thigh and a hip joint of the user during a gait motion. The first structure 20R, 20L may include a first driver 21R, 21L, a first support 22R, 22L, and a first fixer 23R, 23L.

The driver 1310 described above may include the first driver 21R, 21L, and the description of the driver 1310 provided with reference to FIGS. 13 and 14 may be substituted with the description of the first driver 21R, 21L.

The first driver 21R, 21L may be positioned on a hip joint portion of the first structure 20R, 20L and generate a rotational force in various magnitudes in a predetermined direction. A torque generated by the first driver 21R, 21L may be applied to the first support 22R, 22L. The first driver 21R, 21L may be set to rotate within a range of motion of a hip joint of a human body.

The first driver 21R, 21L may operate based on the control signal provided by the main body 10. The first driver 21R, 21L may be implemented by one of a motor, a vacuum pump, and a hydraulic pump. However, example embodiments are not limited thereto.

A joint angle sensor may be provided in a vicinity of the first driver 21R, 21L. The joint angle sensor may detect an angle at which the first driver 21R, 21L rotates about a rotation axis. The sensor 1320 described above may include the joint angle sensor.

The first support 22R, 22L may be physically connected to the first driver 21R, 21L. The first support 22R, 22L may rotate in a predetermined direction with the rotational force generated by the first driver 21R, 21L.

The first support 22R, 22L may be implemented in various shapes. For example, the first support 22R, 22L may be implemented in a shape of a plurality of segments being connected to each other. In this example, a joint may be provided between the segments, and the first support 22R, 22L may be bent by the joint within a predetermined range. In another example, the first support 22R, 22L may be implemented in a shape of a rod. In this example, the first support 22R, 22L may be implemented by a flexible material so as to be bent within a predetermined range.

The first fixer 23R, 23L may be provided on the first support 22R, 22L. The first fixer 23R, 23L may fix the first support 22R, 22L to the thigh of the user.

FIGS. 15 through 17 illustrate an example in which the first support 22R, 22L is fixed to an outer side of the thigh of the user by the first fixer 23R, 23L. When the first support 22R, 22L rotates as the first driver 21R, 21L operates, the thigh to which the first support 22R, 22L is fixed may also rotate in a direction the same as a direction in which the first support 22R, 22L rotates.

The first fixer 23R, 23L may be implemented by one of a band, a belt, and a strap having elasticity, or implemented by a metallic material. FIG. 15 illustrates the first fixer 23R, 23L implemented by a chain.

The second structure 30R, 30L may assist motions of a lower leg and a knee joint of the user during a gait motion.

The second structure 30R, 30L may include a second driver 31R, 31L, a second support 32R, 32L, and a second fixer 33R, 33L.

The second driver 31R, 31L may be positioned on a knee joint portion of the second structure 30R, 30L and generate a rotational force in various magnitudes in a predetermined direction. The rotational force generated by the second driver 31R, 31L may be applied to the second support 32R, 32L. The second driver 31R, 31L may be set to rotate within a range of motion of a knee joint of a human body.

The driver 1310 described above may include the second driver 31R, 31L. The description of the hip joint provided with reference to FIGS. 13 and 14 may similarly apply to the description related to the knee joint.

The second driver 31R, 31L may operate based on the control signal provided by the main body 10. The second driver 31R, 31L may be implemented by one of a motor, a vacuum pump, and a hydraulic pump. However, example embodiments are not limited thereto.

A joint angle sensor may be provided in a vicinity of the second driver 31R, 31L. The joint angle sensor may detect an angle at which the second driver 31R, 31L rotates about a rotation axis. The sensor 1320 described above may include the joint angle sensor.

The second support 32R, 32L may be physically connected to the second driver 31R, 31L. The second support 32R, 32L may rotate in a predetermined direction with the rotational force generated by the second driver 31R, 31L.

The second fixer 33R, 33L may be provided on the second support 32R, 32L. The second fixer 33R, 33L may fix the second support 32R, 32L to the lower leg of the user. FIGS. 15 through 17 illustrate an example in which the second support 32R, 32L is fixed to an outer side of the lower leg of the user by the second fixer 33R, 33L. When the second support 32R, 32L rotates as the second driver 31R, 31L operates, the lower leg to which the second support 32R, 32L is fixed may also rotate in a direction the same as a direction in which the second support 32R, 32L rotates.

The second fixer 33R, 33L may be implemented by one of a band, a belt, and a strap having elasticity, or implemented by a metallic material.

The third structure 40R, 40L may assist motions of an ankle joint and relevant muscles of the user during a gait motion. The third structure 40R, 40L may include a third driver 41R, 41L, a foot rest 42R, 42L, and a third fixer 43R, 43L.

The driver 1310 described above may include the third driver 41R, 41L. The description of the hip joint provided with reference to FIGS. 13 and 14 may similarly apply to the description related to the ankle joint.

The third driver 41R, 41L may be provided on an ankle joint portion of the third structure 40R, 40L and operate based on the control signal provided by the main body 10. The third driver 41R, 41L may also be implemented by a motor, similar to the first driver 21R, 21L or the second driver 31R, 31L.

A joint angle sensor may be provided in a vicinity of the third driver 41R, 41L. The joint angle sensor may detect an angle at which the third driver 41R, 41L rotates about a rotation axis. The sensor 1320 described above may include the joint angle sensor.

The foot rest 42R, 42L may be provided at a position corresponding to a sole of the user and physically connected to the third driver 41R, 41L.

A pressure sensor may be provided on the foot rest 42R, 42L to sense a weight of the user. A sensing result of the pressure sensor may be used to determine whether the user is wearing the walking assistance apparatus 1, whether the user is standing, or whether a foot of the user contacts the ground.

The third fixer 43R, 43L may be provided on the foot rest 42R, 42L. The third fixer 43R, 43L may fix the foot of the user to the foot rest 42R, 42L.

In an example, the third structure 40R, 40L may correspond to the walking assistance apparatus 500 of FIG. 5. For example, the sensor 510 may include the joint angle sensor and the pressure sensor, and the driver 550 may correspond to the third driver 41R, 41L.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A walking assistance method, comprising:
predicting a gait phase of a user within a gait cycle by,
receiving, from a sensor, information related to a motion of the user wearing a walking assistance apparatus,
encoding the information related to the motion to one of a plurality of vertices of a figure with a predetermined shape having i) a preset number of the plurality of vertices corresponding to respective phases of the gait cycle and ii) a continuous perimeter such that a value of the gait cycle remains continuous across a boundary between each of the plurality of vertices corresponding to the respective phases of the gait cycle, the encoding including,
applying the information to a trigonometric function corresponding to the figure to generate at least one vector, and selecting the one of the plurality of vertices on the continuous perimeter of the figure based on the vector boundary, and predicting the gait phase by decoding the selected one of the plurality of vertices to the gait phase such that the gait phase that is predicted is unsmoothed when the selected one of the plurality of vertices crosses the boundary; and controlling an assistance torque applied to the walking assistance apparatus based on the gait phase.

2. The walking assistance method of claim 1, wherein the encoding comprises:

inputting the information into a trained neural network.

3. The walking assistance method of claim 2, wherein the figure is a circle corresponding to the gait cycle.

4. The walking assistance method of claim 1, wherein the controlling comprises:

determining the assistance torque based on the gait phase; and controlling a driver to output the assistance torque.

5. The walking assistance method of claim 4, wherein the determining the assistance torque comprises:

determining a time to apply the assistance torque based on the gait phase; and determining a magnitude of the assistance torque based on the time.

6. The walking assistance method of claim 1, wherein the sensor is on a foot or a shank of the user.

7. The walking assistance method of claim 1, wherein the sensor includes an inertial measurement unit (IMU), and wherein the receiving comprises:

receiving, from the IMU, one or more of acceleration information and rotation velocity information.

8. The walking assistance method of claim 1, wherein the motion of the user includes one or more of a level walking motion, a level running motion, a slope walking motion, and a slope running motion of the user.

9. A non-transitory computer-readable medium comprising computer readable instructions that, when executed by a computer, cause the computer to perform the walking assistance method of claim 1.

10. The walking assistance method of claim 1, wherein the trigonometrical function used to encode the information includes a cosine function and a sine function used to generate determined cosine and sine values of the gait phase, respectively.

11. The walking assistance method of claim 10, wherein the decoding includes performing an arctan operation on the determined cosine and sine values of the gait phase.

12. The walking assistance method of claim 10, wherein the information related to the motion of the user is six-dimensional (6D) information related to measured accelerations and angular velocities of the motion of the user, and the encoding generates a pair of two-dimensional (2D) vectors or a four-dimensional (4D) vector that correspond to the selected one of the plurality of vertices on the continuous perimeter of the figure.

13. The method of claim 2, wherein a value output by the trained neural network at a point in time immediately before a stance phase is started and the value at a point in time at which the stance phase is started is continuous based on a periodicity of the trigonometrical function such that the gait phase remains unsmoothed across the boundary the stance phase and a swing phase.

14. The method of claim 2, wherein the information related to the motion is acceleration information and rotation velocity information and the neural network is trained to map the sensor information indirectly to the gait phase of the user such that the gait phase remains unsmoothed across the boundary a stance phase and a swing phase.

15. A walking assistance apparatus, comprising:

a driver configured to assist walking of a user wearing the walking assistance apparatus; and at least one processor configured to, predict a gait phase of a user within a gait cycle of the user by, receiving, from a sensor, information related to a motion of the user wearing the walking assistance apparatus, encoding the information related to the motion to one of a plurality of vertices of a figure with a predetermined shape having i) preset number of the plurality of vertices corresponding to respective phases of the gait cycle and ii) a continuous perimeter such that a value of the gait cycle remains continuous across a boundary between each of the plurality of vertices corresponding to the respective phases of the gait cycle, the encoding including, applying the information to a trigonometric function corresponding to the figure to generate at least one vector, and selecting the one of the plurality of vertices on the continuous perimeter of the figure based on the vector, and predicting the gait phase by decoding the selected one of the plurality of vertices to the gait phase such that the gait phase that is predicted is unsmoothed when the selected one of the plurality of vertices crosses the boundary, and control an assistance torque applied to the walking assistance apparatus based on the gait phase.

16. The walking assistance apparatus of claim 15, further comprising:

the sensor configured to measure the motion of the user wearing the walking assistance apparatus.

17. The walking assistance apparatus of claim 15, wherein the processor is configured to encode the information by inputting the information into a trained neural network.

18. The walking assistance apparatus of claim 16, wherein the sensor includes an inertial measurement unit (IMU), the IMU being configured to measure one or more of acceleration information and rotation velocity information.

\* \* \* \* \*